United States Patent
Saccomanno (10) Patent No.: US 7,169,311 B2
(45) Date of Patent: *Jan. 30, 2007

(54) APPARATUS FOR DISINFECTING WATER USING ULTRAVIOLET RADIATION

(75) Inventor: Robert J. Saccomanno, Montville, NJ (US)

(73) Assignee: Honeywell International, Inc., Morristown, NJ (US)

(*) Notice: Subject to any disclaimer, the term of this patent is extended or adjusted under 35 U.S.C. 154(b) by 13 days.

This patent is subject to a terminal disclaimer.

(21) Appl. No.: 10/874,293

(22) Filed: Jun. 22, 2004

(65) Prior Publication Data

US 2004/0222163 A1    Nov. 11, 2004

Related U.S. Application Data

(63) Continuation-in-part of application No. 10/268,567, filed on Oct. 9, 2002, now Pat. No. 6,773,584.

(60) Provisional application No. 60/330,174, filed on Oct. 17, 2001.

(51) Int. Cl.
 *C02F 1/32* (2006.01)
(52) U.S. Cl. ................................ 210/748; 422/186.3
(58) Field of Classification Search ............... 210/748, 210/198.1, 205; 422/24, 186.3; 96/224; 250/432 R, 435, 436, 437
See application file for complete search history.

(56) References Cited

U.S. PATENT DOCUMENTS

| | | | |
|---|---|---|---|
| 3,182,193 A | 5/1965 | Ellner | |
| 4,482,809 A | 11/1984 | Maarschalkerweerd | |
| 4,661,264 A | 4/1987 | Goudy, Jr. | |
| 4,968,437 A * | 11/1990 | Noll et al. | 210/748 |
| 5,069,782 A | 12/1991 | Moyher | |
| 5,120,450 A * | 6/1992 | Stanley, Jr. | 210/748 |
| 5,141,636 A * | 8/1992 | Flanagan et al. | 210/209 |
| 5,230,792 A * | 7/1993 | Sauska et al. | 210/97 |
| 5,393,419 A | 2/1995 | Tiede | |
| 5,413,768 A | 5/1995 | Stanley, Jr. | |
| 5,874,741 A * | 2/1999 | Matschke | 250/435 |
| 6,086,760 A * | 7/2000 | Hoffa | 210/205 |
| 6,099,799 A * | 8/2000 | Anderson | 422/24 |
| 6,228,327 B1 | 5/2001 | Matschke | |
| 6,315,963 B1 | 11/2001 | Speer | |
| 6,447,721 B1 | 9/2002 | Horton et al. | |
| 6,552,351 B2 | 4/2003 | Vitt | |
| 2003/0086848 A1* | 5/2003 | Saccomanno | 422/292 |

FOREIGN PATENT DOCUMENTS

| | | |
|---|---|---|
| DE | 43 07 204 A | 9/1994 |
| EP | 0 461 310 | 12/1991 |
| JP | 04 033659 A | 2/1992 |
| JP | 10071189 A | 3/1998 |
| WO | WO 99 52566 A | 10/1999 |
| WO | WO 01 60418 A | 8/2001 |

* cited by examiner

*Primary Examiner*—Frank M. Lawrence
(74) *Attorney, Agent, or Firm*—Oral Caglar, Esq.

(57) ABSTRACT

Ultraviolet radiation is used to disinfect water in a flow tube, where the flow tube acts as a fluid filled light guide for the ultraviolet radiation and the ultraviolet radiation propagates through the flow tube via total internal reflection.

17 Claims, 11 Drawing Sheets

| Avg path length (in) | 4.5 | | | | | |
|---|---|---|---|---|---|---|
| Water absorption (1/cm) | 0.3 | 0.125 | 0.05 | 0.02 | 0.01 | 0.008 |
| Average dosage factor (area under curve divided by length) | | | | | | |
| TIR | 0.0049 | 0.0202 | 0.0674 | 0.1889 | 0.3520 | 0.4123 |
| AL | 0.0041 | 0.0161 | 0.0466 | 0.1006 | 0.1490 | 0.1637 |
| SS | 0.0014 | 0.0043 | 0.0081 | 0.0112 | 0.0126 | 0.0129 |
| Ratio between TIR and AL or SS | | | | | | |
| TIR/AL | 1.18 | 1.25 | 1.45 | 1.88 | 2.36 | 2.52 |
| TIR/SS | 3.45 | 4.63 | 8.29 | 16.92 | 27.99 | 31.99 |

FIG. 11

| Avg path length (in) | 2.25 | | | | | |
|---|---|---|---|---|---|---|
| Water absorption (1/cm) | 0.3 | 0.125 | 0.05 | 0.02 | 0.01 | 0.008 |
| Average dosage factor (area under curve divided by length) | | | | | | |
| TIR | 0.0154 | 0.0512 | 0.1494 | 0.3520 | 0.5365 | 0.5901 |
| AL | 0.0126 | 0.0370 | 0.0857 | 0.1490 | 0.1910 | 0.2018 |
| SS | 0.0036 | 0.0072 | 0.0105 | 0.0126 | 0.0134 | 0.0136 |
| Ratio between TIR and AL or SS | | | | | | |
| TIR/AL | 1.23 | 1.38 | 1.74 | 2.36 | 2.81 | 2.92 |
| TIR/SS | 4.25 | 7.07 | 14.16 | 27.99 | 40.08 | 43.52 |

APPARATUS FOR DISINFECTING WATER USING ULTRAVIOLET RADIATION

RELATED APPLICATIONS

This application is a continuation-in-part of my application Ser. No. 10/268,567, filed Oct. 9, 2002, now U.S. Pat. No. 6,773,584, Aug. 10, 2004, and which is entitled to the benefit of Provisional Application Ser. No. 60/330,174, filed Oct. 17, 2001.

BACKGROUND OF THE INVENTION

1. Technical Field

This invention relates to a water purification system using intense ultraviolet irradiation to break down chemical bonds in toxic compounds and to de-activate pathogens. The method can also be applied to any mass transport, including the purification of air. These systems can be applied to purify fluids containing naturally occurring toxins or those resulting from biological and chemical agents used in warfare.

2. Background Art

The first application of an ultraviolet (UV) low-pressure mercury vapor discharge lamp to disinfect water was in Marseilles, France in 1901. However, it was not until 1955 that UV disinfection became widely applied in Europe for potable water. In that year UV disinfection equipment was installed in Switzerland, Austria and Norway. Following the discovery of the formation of halogenated hydrocarbons during chlorination, UV disinfection since became popular in most European countries.

U.S. Pat. No. 1,196,481, issued Aug. 29, 1916 described the use of a mercury vapor lamp to generate sufficient ultraviolet light (mostly 254-nm wavelength) to purify water. Further refinements have been made over the years, such as in Ellner U.S. Pat. No. 3,182,193 issued May 4, 1965, Maarschalkerweerd U.S. Pat. No. 4,482,809 issued Nov. 13, 1984, Moyher U.S. Pat. No. 5,069,782 issued Dec. 3, 1991, Tiede U.S. Pat. No. 5,393,419 issued Feb. 28, 1995, and Anderson U.S. Pat. No. 6,099,799 issued Aug. 8, 2000. Much of the latter art referenced above improved upon aspects related to commercial viability, such as improving UV dosage uniformity through the use of baffles, UV-transparent coils, and controlled turbulence; increasing UV intensity for higher flow rates by increasing the number of lamps in a given volume; and improving maintenance through the use of Teflon coatings, wiper mechanisms, and adding turbulence.

Central to the present invention is the maximization of UV contact-time with the water, as opposed to being absorbed by the walls of the container.

It's well known to those familiar with the art that many of the UV water disinfecting systems utilize stainless steel water jackets, owing at least in part to its history of use in fluid applications requiring sanitary operation. It's viability as an efficient UV reflector, however, is marginal, with data showing less than 40% reflectance at normal for the germicidal wavelengths around 250 nm (J. Zwinkels, et al, pgs 7933–7944, Applied Optics, Vol. 33, No. 34, 1 Dec. 1994).

Prior art portable UV disinfection systems are described, for example, in U.S. Pat. No. 5,900,212 as well as PCT publication WO 01/28933. The '212 utilizes a portable UV source placed in a container whose walls are of unknown reflectance. In the PCT publication, a UV-transparent window allows sunlight through, only to strike the container walls, again of unkown reflectance.

Improvements in reflectance is discussed in Stanley Jr, U.S. Pat. No. 5,413,768, whereby water is guided through a high tensile strength container having an interior surface that is highly reflective to UV (such as aluminum). The container is further lined with an FEP layer up to 10 mm thick and anchored to the container, for example via ridges formed by routing the interior of the container. While FEP is generally thought to be transmissive in the UV, it will be shown that thick layers are in fact absorptive.

It will be shown that in applications where the water being irradiated is "polished", the walls of prior art systems absorb a high proportion of the incident UV.

It will also be shown that in the present invention, there is substantial efficiency benefits in using total internal reflection as the primary means of maximizing contact time between UV and the fluid.

SUMMARY OF THE INVENTION

My invention is an apparatus and method for disinfecting water, or other fluid, that channels water through a tube and couples ultraviolet (UV) energy from a high intensity lamp into the tube in a direction generally parallel to the flow of water. The water, or other fluid, acts like the core of a liquid light pipe/guide, with a low index cladding surrounding the water, either via a low-index coating inside a tube, an air gap adjacent to a UV-transparent tube, or some other cladding mechanism as is known in the art of liquid light guides, such as that taught in U.S. Pat. No. 4,009,382, U.S. Pat. No. 6,163,641, U.S. Pat. No. 6,418,257, U.S. Pat. No. 6,507,688 and WO00/10044. In the case where the cladding is not deposited on the inside of the tube, then the tube itself is constructed of a non-UV-absorbing material, such as UV-grade fused silica glass or a non-absorbing polymer tubing (optionally reinforced to preclude bursting, for example as taught in U.S. Pat. No. 5,371,934 and U.S. Pat. No. 6,620,190). Advantageously, the use of light-pipe technology, which is based on total internal reflection (TIR), ensures that all the input UV radiation is dissipated in the water. Preferably, the tube is polygonal in cross-section which is known, for example in the art of projection display systems, to maximize light flux uniformity within a light pipe over a shorter distance than one having a circular cross section.

Embodiments of my invention with multiple zones efficiently handle a wide range of water absorption coefficients, all at the highest practical efficiency. In accordance with an aspect of one embodiment of my invention, as disclosed in my patent application, one of three zones is defined by a concentric UV-grade tubing concentrically around only a portion of the tube through which the water flows and others of these zones are defined between these tubes and the enclosing outer tube.

In a second embodiment of my invention, in which fluid enters at one end of my apparatus and exits at the other end, an air gap surrounds the entire inner tube through which the water flows. The total internal reflections in accordance with my invention are assured by the relative refractive indices of the fluid, the inner tube defining the fluid chamber through which the fluid flows, and the gap between that inner tube and the inner surface of the outer housing.

In a third embodiment of my invention the fluid chamber through which the fluid to be disinfected flows comprises a hollow helical coil, with the ultraviolet radiation being guided through the hollow helical coil by total internal reflection. In this embodiment the ultraviolet radiation can be introduced by a side-coupled source of the ultraviolet radiation. To ensure maximum efficiency, the bend radius of the hollow helical coil is sufficiently greater than the coil diameter, a parameter known to affect light leakage in the art of fiber optics.

In a further embodiment of my invention, a portable canteen system comprises a container for an untreated fluid, such as water, with the outlet from the container passing through a cap that comprises a coiled tubing into which ultraviolet radiation is launched, the radiation being guided through the coiled tubing by total internal reflection, in accordance with my invention.

In accordance with an aspect of my invention, the relative refractive indices are such that the ultraviolet radiation proceeds within the fluid chamber of the various embodiments of my invention substantially solely by total internal reflection. Specifically, the water or other fluid to be treated has a refractive index of n1 and the wall or walls defining the fluid chamber have a refractive index of n2, with n2 being less than n1. The refractive indices can be considered to define a numerical aperture, where the term 'numerical aperture' describes the ability in an optical system to accept rays. The ultraviolet radiation coupled into the apparatus of my invention is substantially within the numerical aperture defined by the relative refractive indices n1 and n2.

BRIEF DESCRIPTION OF DRAWINGS

Brief Description of the Severals Views of the Drawing

LIST OF REFERENCE NUMBERS FOR THE MAJOR ELEMENTS IN THE DRAWING

The following is a list of the major elements in the drawings in numerical order.
1 incidence angle (refraction at fluid inlet tube internal surface)
2 internal reflection angle (reflection at fluid inlet tube external surface)
5 fluid (to be disinfected)
10 fluid inlet tube
11 entrance end (fluid inlet tube)
12 exit end (fluid inlet tube)
13 internal surface (fluid inlet tube)
14 external surface (fluid inlet tube)
15 concentric gap (between inlet tube and optical cladding tube)
20 optical cladding tube
30 fluid containment vessel
31 ultraviolet mirror (fluid containment vessel internal surface)
32 air gap (fluid containment vessel)
33 inner tube (of fluid containment vessel)
35 ultraviolet inlet aperture
36 lower ultraviolet window surface
37 upper ultraviolet window surface
40 high intensity ultraviolet lamp
50 fluid outlet tube
71 first UV light ray (exiting lower ultraviolet window surface)
72 second UV light ray (exiting fluid)
73 third UV light ray (entering fluid inlet tube internal surface)
74 fourth UV light ray (exiting fluid inlet tube internal surface)
75 fifth UV light ray (entering fluid)
80 vessel
81 inlet nozzle (of vessel)
83 exit port (of vessel)
85 surface (inner wall)
86 inner UV transmissive tube
87 window
88 lamp
75 fifth UV light ray (entering fluid)
100 light pipe (formed from fluid, fluid inlet tube, and concentric gap)
101 stainless steel support structure
181 aperture shaped water inlet
182 aperture shaped water outlet
185 UV sidewall glass mirror
186 mirror coated UV window
187 apertured aluminum mirror coated UV window
188 ultraviolet radiation source
191 pressurized water cavity
202 non-UV absorbing coupling prism
210 coiled tubing (high refractive index)
220 surrounding medium (low refractive index)
281 water inlet (to coiled tubing)
282 water outlet (from coiled tubing)
295 input UV radiation
300 canteen
301 screw cap (for canteen)
302 fill tube (p/o canteen)
303 air vent tube (p/o canteen)
304 water-blocking/air-passing membrane vents (cover air vent tube)
310 coiled tubing (high refractive index)
381 water inlet (to coiled tubing)
391 water (contained within canteen)
392 air (introduced into canteen)
r ratio of bend radius of the coil to radius of (coiled) tubing
R light pipe (formed from fluid, fluid inlet tube, and concentric gap)

DESCRIPTION OF THE INVENTION

Mode(s) for Carrying Out the Invention

Figure 1:
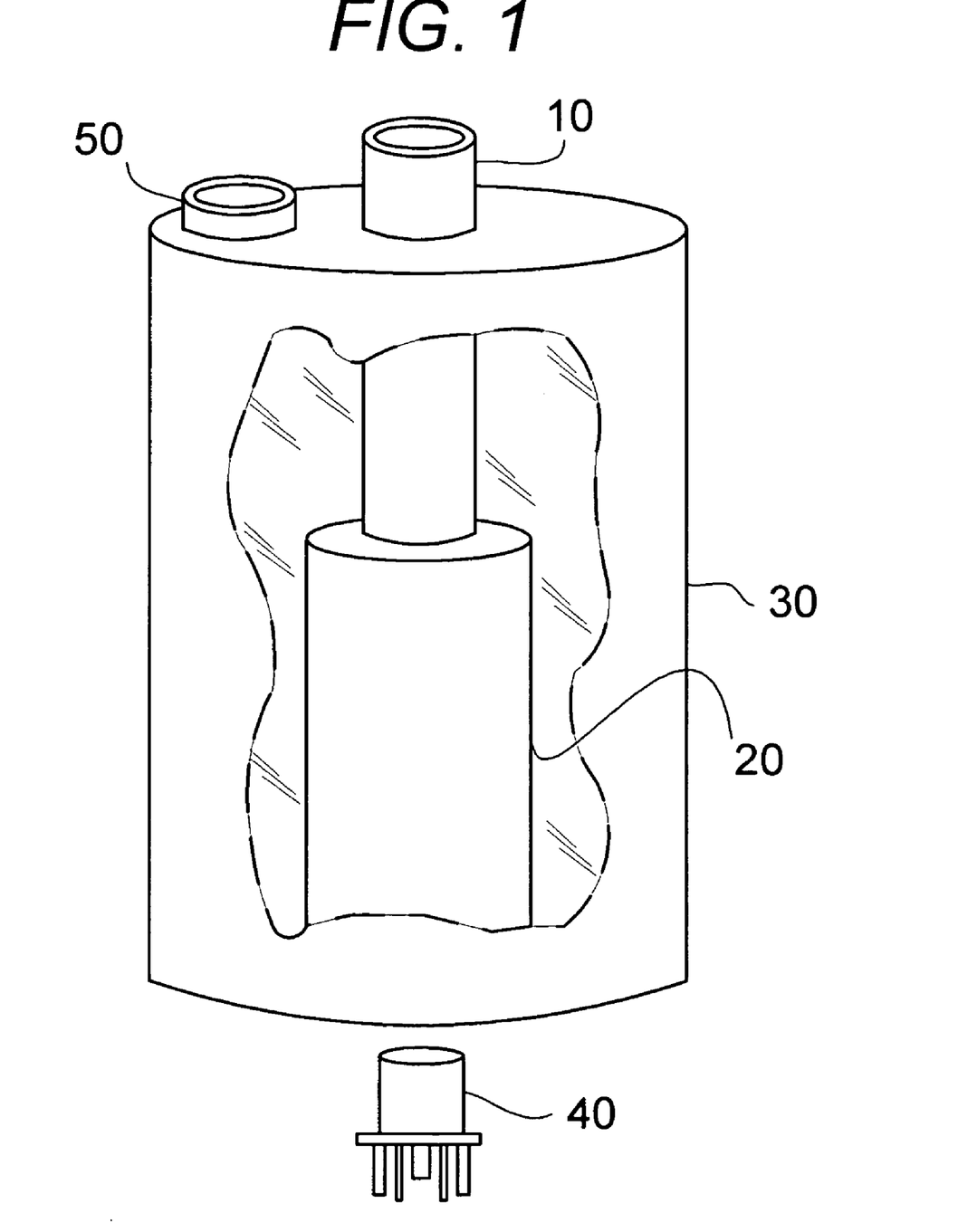
FIG. 1 depicts an apparatus for disinfecting water using ultraviolet radiation (UV) in accordance with one illustrative embodiment of my invention.

Referring first to FIG. 1, the basic construction of an ultraviolet (UV) water disinfecting device in accordance with a first embodiment of my invention is shown, including a fluid inlet tube 10 that acts as a central light pipe, an optical cladding tube 20 around the lower portion of fluid inlet tube 10 and defining therewith a concentric gap 15 (seen in FIG. 2), a fluid containment vessel 30, a fluid outlet tube 50, and a high intensity UV lamp 40, such as a flashlamp.

Figure 2:
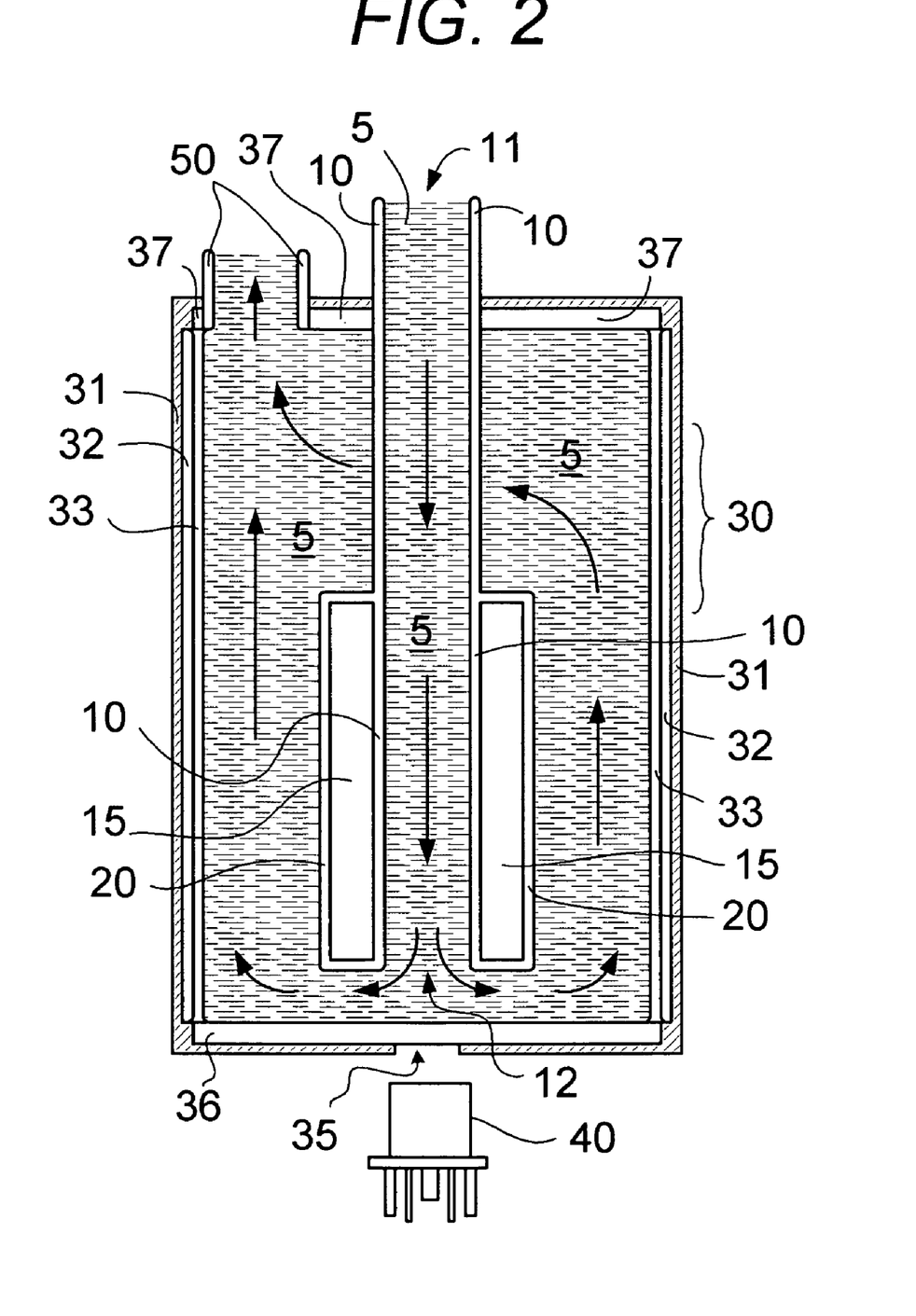
FIG. 2 depicts a sectional view of the UV disinfecting apparatus of FIG. 1.

Referring next to FIG. 2, the fluid containment vessel 30 includes an internal surface configured as an ultraviolet mirror 31; for example, the fluid containment vessel may be constructed from aluminum and the internal surface may be polished aluminum. A fluid 5 to be disinfected, such as water, enters the fluid inlet tube 10 through an entrance end 11. The fluid inlet tube 10 may be manufactured, for example from UV-grade fused silica.

The fluid 5 travels through the fluid inlet tube 10 towards the high intensity UV lamp 40 and exits the fluid inlet tube 10 at the exit end 12. The fluid 5 flow then strikes an ultraviolet (UV) window lower surface 36, which forms a portion of the lower end of fluid containment vessel 30. Next, the fluid 5 flow is redirected to the fluid outlet tube 50, which is located in the upper end of the fluid containment vessel 30.

The fluid 5 is contained within the fluid containment vessel 30. The fluid containment vessel 30 includes an inner tube 33, which may be constructed from UV-grade fused silica, contained within an outer aluminum shell with a reflective interior surface defining a UV mirror 31, with an air gap 32 between the outer shell and the inner tube 33. Then ends of the outer tube 30 are closed off with the lower ultraviolet window surface 36 and an ultraviolet window upper surface 37.

The preferred orientation of the ultraviolet (UV) water disinfecting device is vertical, so that the fluid 5 flow approximates plug-flow, and the position of the fluid outlet tube 50 is oriented to allow for quick and efficient removal of undesirable air bubbles. Air bubbles present (e.g. induced by pump vanes) in the fluid 5 can form scattering sites for the UV radiation thereby degrading system efficiency. These UV scattering sites result in UV radiation being directed at less than optimum angles causing reflections from the fluid containment vessel internal surface, the ultraviolet mirror 31 that is approximately 86% reflective when composed of aluminum tube. Without these UV scattering sites, the ultraviolet radiation is dissipated mostly within the fluid 5, because all reflections are near loss-less due to of the total internal reflection (TIR) operation of a light pipe. There is, however, a side-benefit from a degree of scattering, and that is an improvement in the uniformity of the UV light throughout the device, the theory of which is described in "*Brighter Backlights Using Highly Scattered Optical-Transmission Polymer*" (Horibe, et al, pg. 379–381, Society of Information Display, paper 24.2, SID 1995 Digest). The degree of scattering can be optimized, for example, using any suitable ray-trace program, such as ASAP from Breault Research (Tucson, Ariz.).

Figure 3:
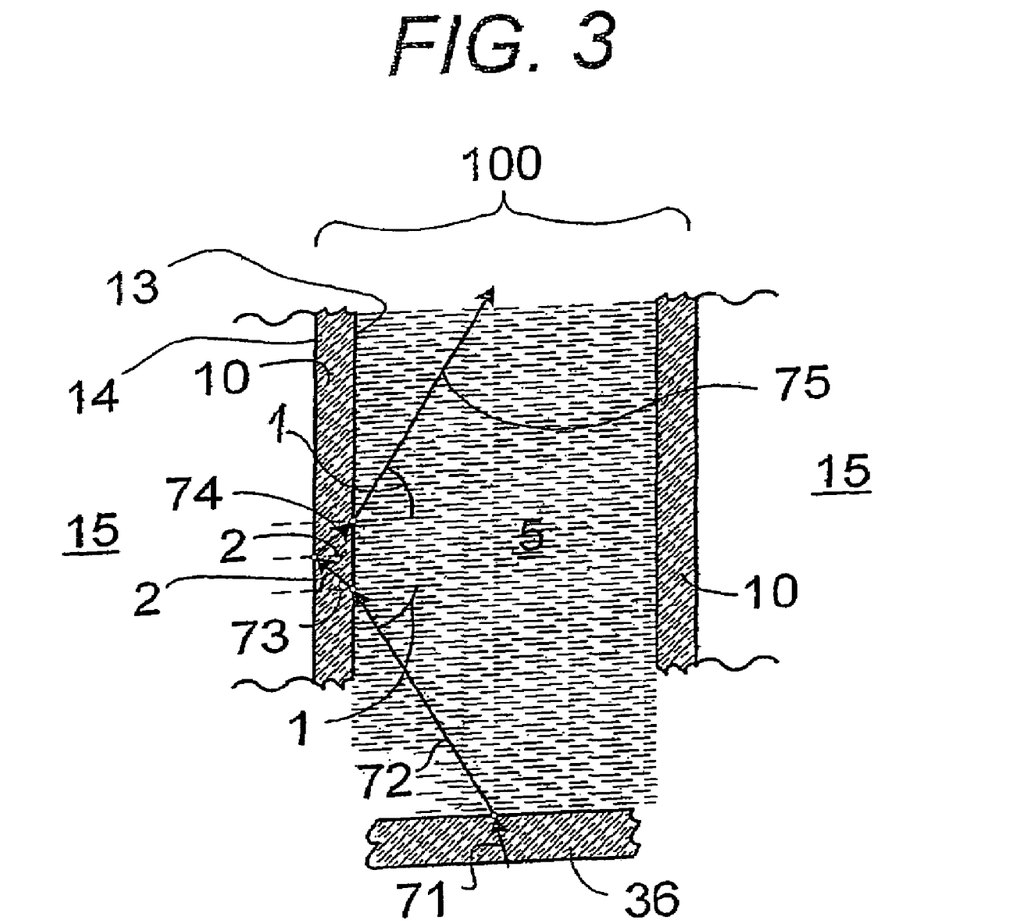
FIG. 3 depicts a light pipe irradiation zone within the UV disinfecting apparatus of FIG. 1, showing how the ultraviolet radiation is contained using total internal reflection (TIR).

Referring next to FIG. 3, a light pipe 100 region is formed from the fluid 5, such as water, the fluid inlet tube 10, such as a UV-grade fused silica tube, and the concentric gap 15, such as an air gap or a vacuum gap. The concentric gap 15 is hydraulically isolated from the fluid 5, in order to allow the light pipe 100 to operate. Light pipe operation is based on the refractive index of the concentric gap being less than the refractive index of the fluid 5. The refractive indices of fused silica and water in the UV region of the light spectrum are shown in Table 1 below.

TABLE 1

Refractive Indices of Fused Silica and Water

| Fused Silica UV Grade (SiO2) | | Water | |
|---|---|---|---|
| Wavelength (nm) | Refractive Index | Wavelength (nm) | Refractive Index |
| 170 | 1.615 | 172 | 1.568 |
| 185 | 1.575 | 185 | 1.492 |
| 200 | 1.550 | 200 | 1.452 |
| 214 | 1.534 | 215 | 1.427 |
| 280 | 1.494 | 280 | 1.379 |
| 302 | 1.487 | 305 | 1.370 |
| 436 | 1.467 | 450 | 1.344 |
| 546 | 1.460 | 550 | 1.336 |
| 656 | 1.456 | 650 | 1.331 |

As shown in Table 1, water has a lower refractive index than UV grade Silica glass in the ultraviolet (UV) portion of the light spectrum.

Ultraviolet radiation is transmitted from the high intensity ultraviolet lamp 40, passes through the ultraviolet inlet aperture 35, and enters the lower ultraviolet window surface 36 as shown in FIG. 2. A first UV light ray 71 exits lower ultraviolet window surface, is bent by refraction, and enters the fluid 5, defining a second UV light ray 72. The second UV light ray 72 impinges upon the internal surface 13 of the fluid inlet tube 10, which is in contact with the fluid 5, at an incidence angle 1, where incidence angle 1 is measured with reference to the surface normal of internal surface 13. As the second UV light ray 72 enters a sidewall of the fluid inlet tube 10, it is bent by refraction and redirected at a new internal reflection angle 2, defining a third UV light ray 73.

The value of angle 2 is a function of incident angle 1 and the refractive indices of the fluid 5 and the material, such as UV-grade silica, from which the fluid inlet tube 10 is constructed. The third UV light ray 73 continues through the fluid inlet tube 10 material and impinges upon the external surface 14 of the fluid inlet tube that is in contact with the concentric gap 15. The third UV light ray 73 is reflected back into the sidewall of the fluid inlet tube 10, defining a fourth UV light ray 74 when the refractive indices of the fluid inlet tube 10 material and the concentric gap 15 meet certain conditions as defined by Snell's Law. The refractive index of the concentric gap 15 is defined by the material contained in the concentric gap or by the refractive index of a vacuum if no material is contained within the concentric gap 15.

It is a feature of the first embodiment of my invention that a light pipe 100 region exists for at least part of the length of the fluid inlet tube 10. Therefore, it is required that the incidence angle 2 be limited to a predetermined range in accordance with the refractive indices of the fluid 5, the material from which the fluid inlet tube 10 is constructed, and the concentric gap 15. In a preferred embodiment of my invention, the fluid inlet tube 10 is constructed from UV-grade silica glass, the fluid 5 to be disinfected is water, and the concentric gap 15 contains a vacuum.

Figure 4:
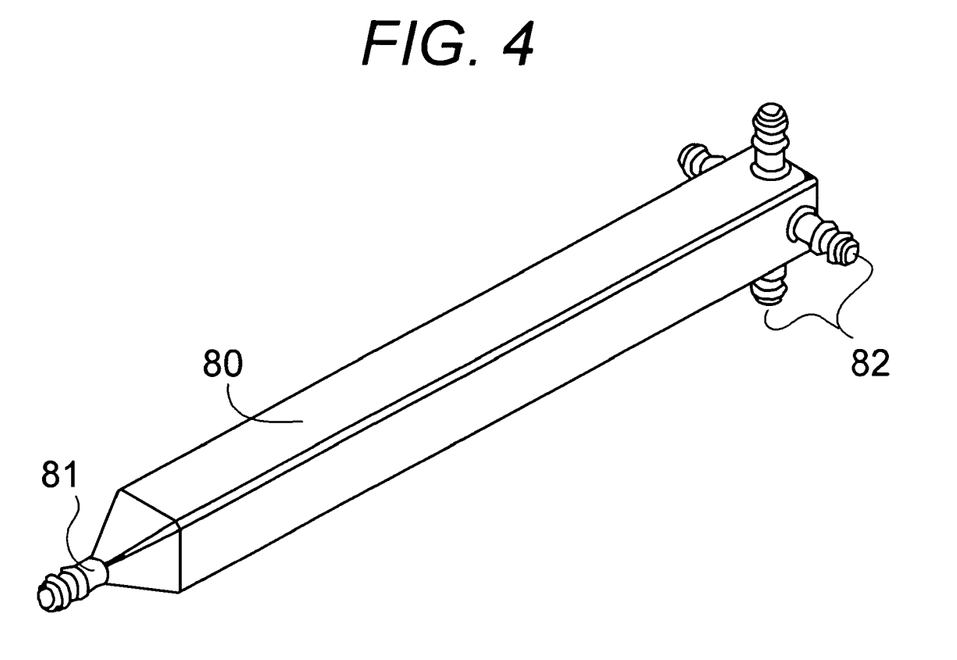
FIG. 4 depicts an apparatus for purifying or disinfecting a fluid, such as water, using ultraviolet radiation in accordance with a second illustrative embodiment of my invention.
Figure 5:
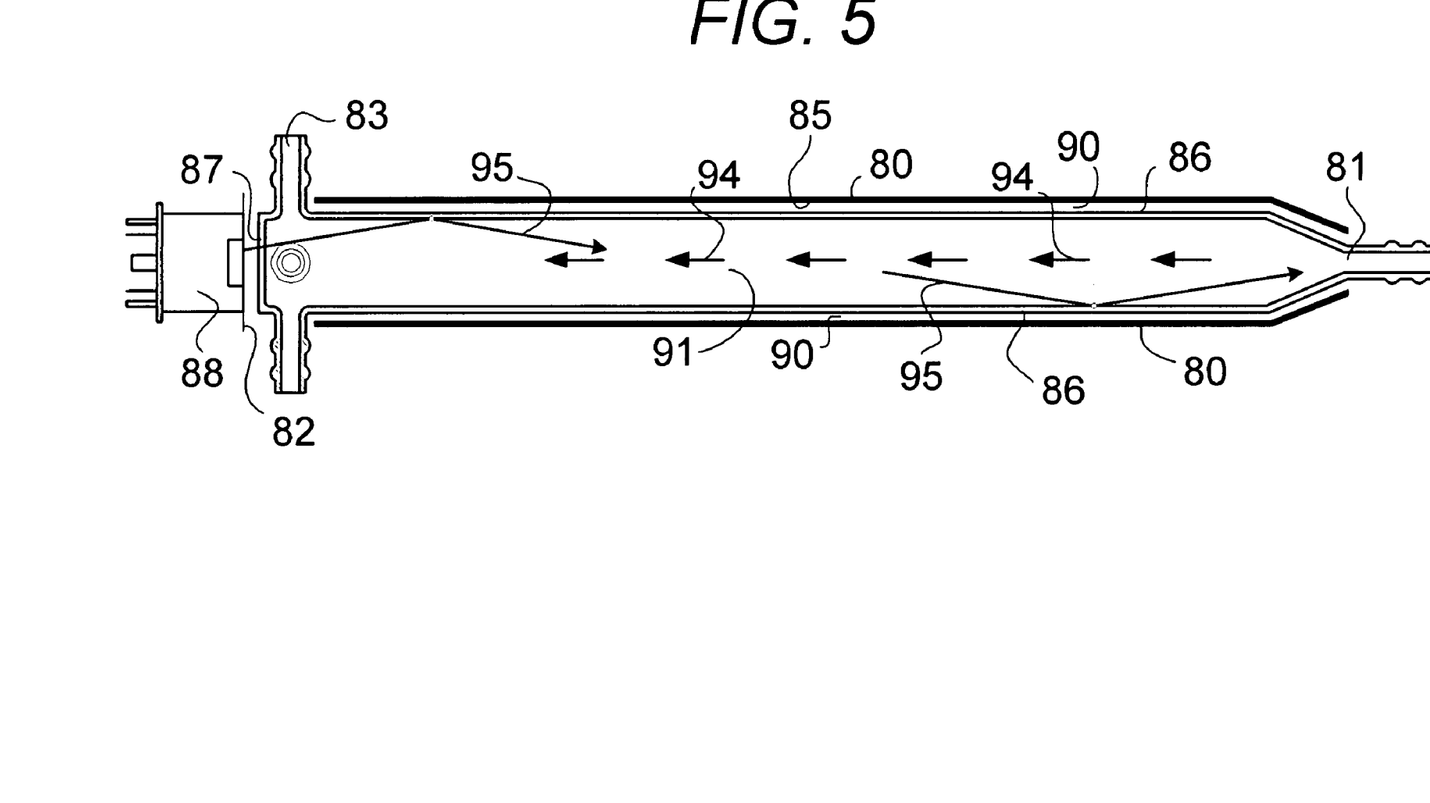
FIG. 5 depicts a sectional view of FIG. 4.

Turning now to FIGS. 4 and 5, there is depicted a second embodiment of my invention, wherein, unlike the first embodiment, the fluid, such as water, enters my apparatus at one end thereof and exits from the other end. The apparatus comprises an outer containment vessel 80, which may as depicted have a square or polygonal cross section or be of tubular or other configuration, and which is advantageously of a metal with reflective inner wall surface or surfaces 85, such as made from mirror-finished anodized aluminum. At one end the vessel 80 has an input nozzle 81 for receiving the fluid to be purified or disinfected, and at the other end are four exit ports 83, each located on one of the four sides of the vessel 80. Note that light pipes having square or polygonal cross sections are known to homogenize light over a shorter distance than circular-cross section light pipes (see U.S. Pat. Nos. 3,170,980 and 5,341,445 as well as "*The Use of a Kaleidoscope to Obtain Uniform Flux Over a Large Area in a Solar Arc Imaging Furnace*", M. M. Chen et al., Applied Optics, March 1963, Vol. 2, No. 3), and so certain applications may benefit from this geometry, although such a geometry may be more expensive to fabricate than circular light pipes.

As seen in FIG. 5, located within the vessel 80 and sealed thereto is an inner UV transmissive tube 86, which may also be either square or tubular, which advantageously may be of UV-grade fused silica, and which defines the fluid chamber 91 of this embodiment. The inner UV transmissive tube 86 has a glass window 87 at its base and against which an ultraviolet flash lamp 88 is pressed to minimize absorption in air of the ultraviolet wavelengths below 200 nanometers (see FIGS. 10, 11a & 11b).

The inner UV transmissive tube 86 thus defines the fluid chamber 91 for my apparatus and with the inner surface or surfaces 85 of the vessel 80 defines a gap 90 which advantageously is kept to a minimum size while avoiding any contact between the inner surface 85 of the vessel 80 and the inner UV transmissive tube 86. The tube 86 and the gap 90 define walls for the fluid chamber 91. Advantageously, the inner UV transmissive tube 86 also has a minimal glass thickness consistent with sufficient strength to resist breakage, the minimal thickness minimizing ultraviolet absorption within the glass tubing. The minimal thickness of the inner UV transmissive tube 86 can be helped with supplemental internal support for the tubing, however such support must avoid interfering with the total internal reflections of the ultraviolet radiation within the inner tubing fluid chamber 91. As an example, a narrow wire can be wrapped around the outside of the glass tubing, having only point-contacts with the glass. An aluminum reflector is then wrapped around the wire, thereby forming an air gap between the aluminum and the glass, preserving TIR. The structure can be further supported by a pressure-containing structure (e.g. steel tube), which can be compressed against the aluminum via a thin compliant material to accommodate the differences in expansion & contraction of the various materials.

The gap 90 between the inner surface of the inner internally reflecting inner surface of the housing or vessel 80 and the outer surface of the inner UV transmissive tube 86, which also serves as a fluid chamber, advantageously contains a vacuum or may be filled with a material assuring a refractive index of less than the refractive index of the fluid passing within the inner UV transmissive tube 86.

As with my first embodiment, the water or fluid to be purified has a first refractive index while inner UV transmissive tube 86 which defines the fluid chamber 91 for the water or other fluid has a second refractive index, with the gap 90 between the inner surface 85 of the housing and the inner UV transmissive tube 86 having a third refractive index. These first, second, and third refractive indices are such that the ultraviolet radiation is propagated within the inner UV transmissive tube 86 defining the fluid chamber 91 via total internal reflection. As depicted in FIG. 5, arrows 94 show the fluid flow while the total internally reflected ultraviolet radiation is shown by arrows 95 going in the opposite direction to the arrows 94. Specifically, the fluid has a refractive index n1 and the walls of the fluid chamber comprising the tube 86 and the gap 90 have a collective refractive index n2 with n2 being less than n1.

Figure 6:
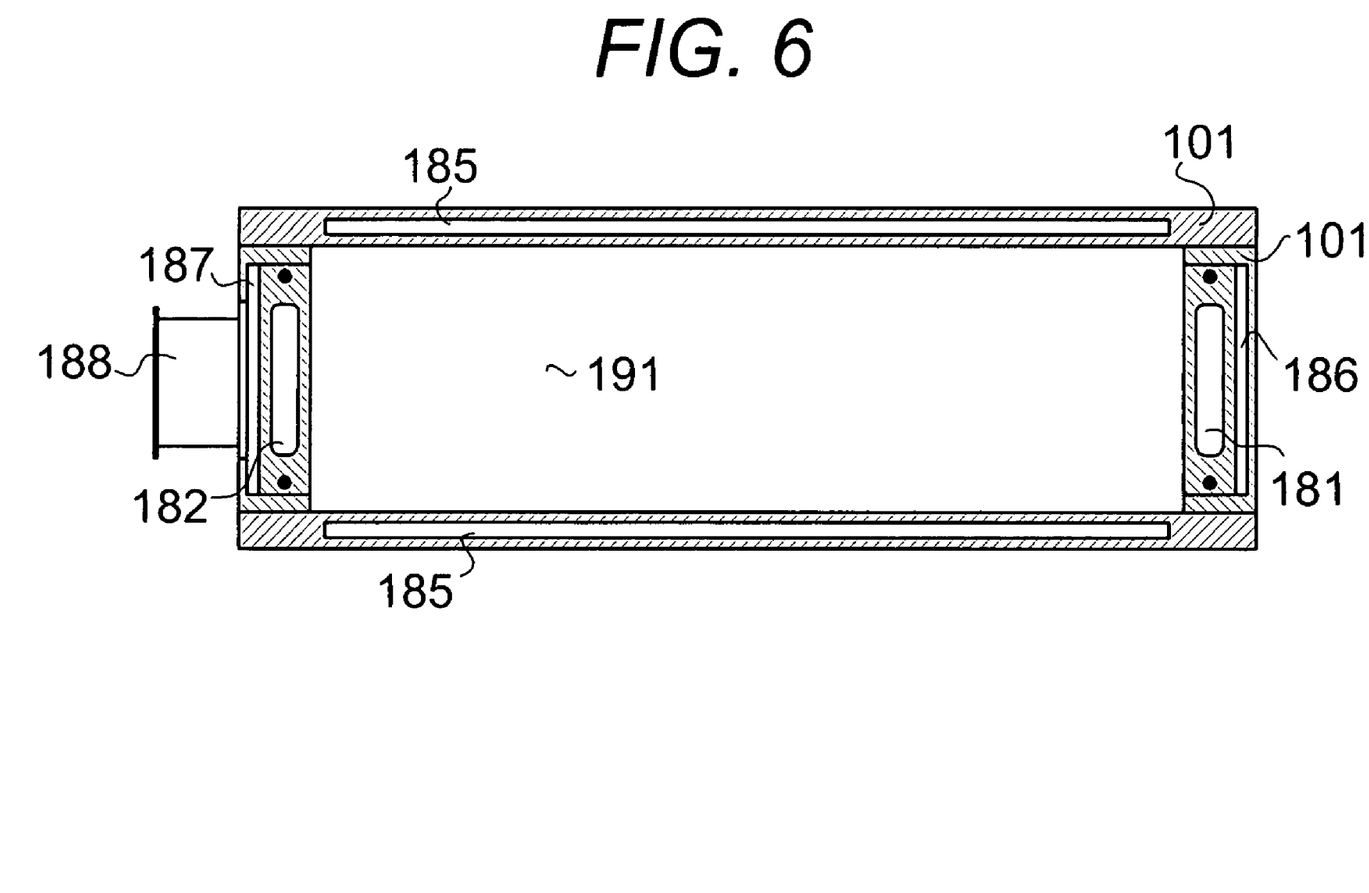
FIG. 6 depicts an embodiment comprises plate-like elements as opposed to the constructions shown in FIGS. 4 & 5.

Referring now to FIG. 6, there is shown an alternate embodiment of the present invention comprising a plate-and-frame construction. Water flows into pressurized water cavity 191 through one of the slotted aperture shaped water inlets 181. After ultraviolet (UV) irradiation as described above, water exits the pressurized water cavity 191 via one of the slotted aperture shaped water outlets 182. In one embodiment, there are four slotted aperture shaped inlets 181 and four slotted aperture shaped outlets 182 where each of these inlets and outlets is connected to a stainless steel adapter that includes standard threads for hose fittings to potable water sources.

The pressured water cavity 191 is formed by stainless steel support structure 101, which includes several windows cut therethrough. Each of these windows is installed from within the pressurized water cavity 191 region so that during operation, water pressure forces a seal between the windows and the stainless steel support structure 101. The ultraviolet radiation (UV) source 188, such as a xenon lamp is mounted adjacent to the stainless steel support structure 101 at the outlet port 182 region and the UV radiation emitted therefrom enters the pressurized water cavity 191 through an apertured aluminum mirror coated UV window 187 bonded in a groove portion of the stainless steel support structure 101. At the inlet port 181 region of the stainless steel support structure 101 a mirror coated UV window 186 with an aluminum coating on the air side is bonded in a groove. UV sidewall glass mirrors 185 are bonded in grooves contained within sidewalls of the stainless steel support structure 101. In a further embodiment, all metal to glass and metal to metal joints are sealed with caulk and/or adhesive.

Figure 7:
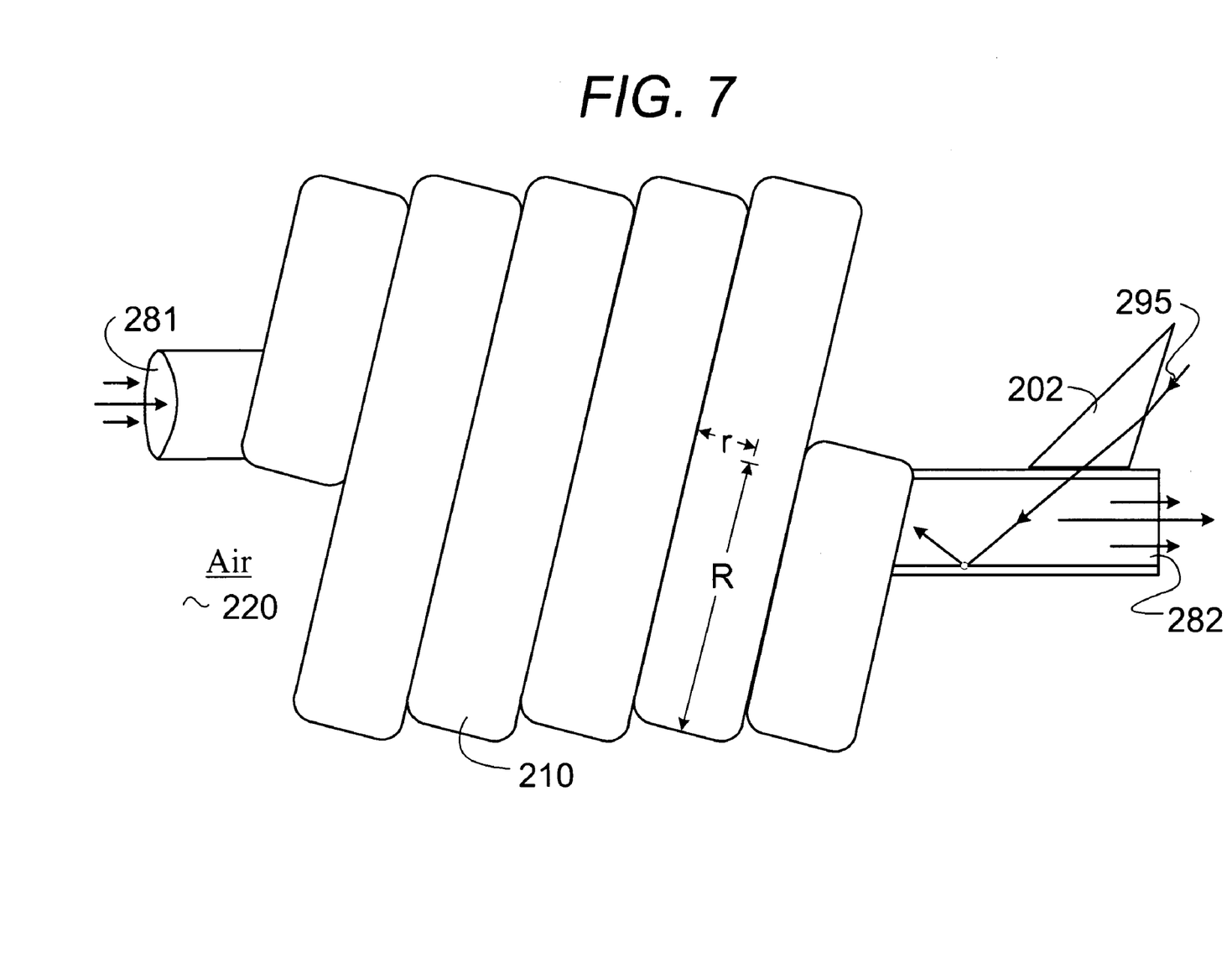
FIG. 7 depicts a coiled-configuration showing UV entering via a side-coupling optic

In FIG. 7, there is shown a further embodiment of my invention comprising a hollow helical coiled light pipe construction with a side-coupling optic that is similar to a configuration taught in U.S. Pat. No. 6,263,003. Alternate side-coupling techniques are also taught in U.S. Pat. Nos. 5,058,980, 5,923,694, 6,370,297, and 6,625,354. For a coiled UV disinfection system, such as the embodiment shown in FIG. 7 the losses due to TIR leakage are useful in determining the source power required for the input UV radiation 295. More specifically, the embodiment of FIG. 7 shows input UV radiation 295 being coupled into coiled tubing 210 via a non-UV absorbing coupling prism 202. The UV radiation is contained within the coiled tubing 210 by TIR because the material of the coiled tubing 210, such as UV-grade fused silica glass, has a higher refractive index than the surrounding medium 220, such as air or a vacuum. The ratio r between the bend radius of the coil and the coiled tubing radius R is advantageously is greater than 5:1 in order to ensure high efficiency.

The coiled light pipe embodiment shown in FIG. 7 disinfects water that flows in through water inlet 281, circulates through coiled tubing 210, and exits through water outlet 282. Such disinfection is accomplished by exposing biological material contained within the water to the ultraviolet radiation that is conducted by total internal reflection (TIR) in accordance with my invention and as described above. As is well known, such biological material includes nucleic acid components such as deoxyribonucleic acid (DNA) or ribonucleic acid (RNA).

If the operating pressure of fluids to be disinfected is high enough, the coiled tubing 210 may be strengthened to preclude the coil from rupturing. An example strengthening material is an exterior wire braid. In a preferred embodiment, the external wire braid is further wrapped with aluminum foil to recycle TIR-leakage back into the fluid.

Figure 8:
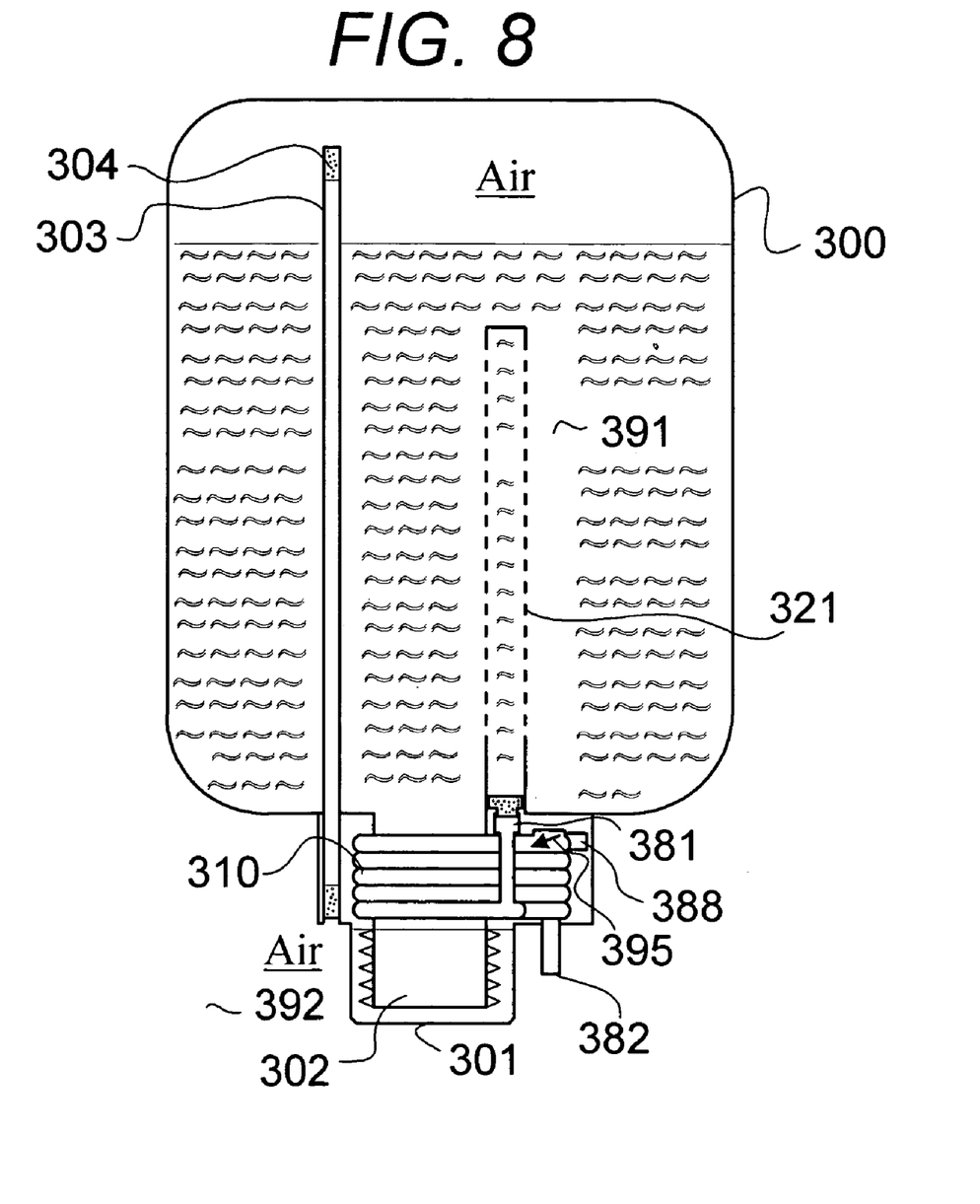
FIG. 8 depicts a canteen using a coiled-configuration

Referring now to FIG. 8, there is shown a further illustrative embodiment of my invention comprising a canteen 300 with a screw cap 301 covering an inlet fill tube 382. A coiled tube 310 circumferentially surrounds the fill tube 302. In operation, the canteen 300 is filled with water 391 via the fill tube 302. Advantageously, the fill tube 302 can be fitted with a filter (not shown).

Water 391 contained within canteen 300 is disinfected by ultraviolet radiation 395 emitted from UV source 388, such as a UV light emitting diode (LED) or laser diode as follows. The water 391 enters the coiled tubing 310 via water inlet 381 which is optionally provided with a sediment filter 321 such as wire mesh filters avialable from Genesis Filtration Inc. (Rancho Cucamonga, Calif.) and Martin Kurz & Co., Inc. (Mineola, N.Y.). In order to allow water 391 to enter the water inlet 381, air 392 is introduced into the canteen 300 via air vent tube 303 which has water-blocking/air-passing membrane vents 304 at both ends. A suitable water-blocking/air-passing membrane is available from obtained from W. L. Gore & Associates, Inc (Fenton, Mo.). Purified water exits the coiled tubing 310 (as well as the canteen 300) via water outlet 382. During periods when the canteen is not providing water, a screw cap or other suitable shutoff is fitted to water outlet 382.

The main UV-water interaction occurs by total internal reflection (TIR) within the coiled tubing 310 as previously described for FIG. 7. In the particular embodiment shown in FIG. 8, the ultraviolet radiation 395 is end-launched into the coiled tubing 310, although other embodiments are contemplated that use side-launched ultraviolet radiation, such as shown in FIG. 7.

Figure 9:
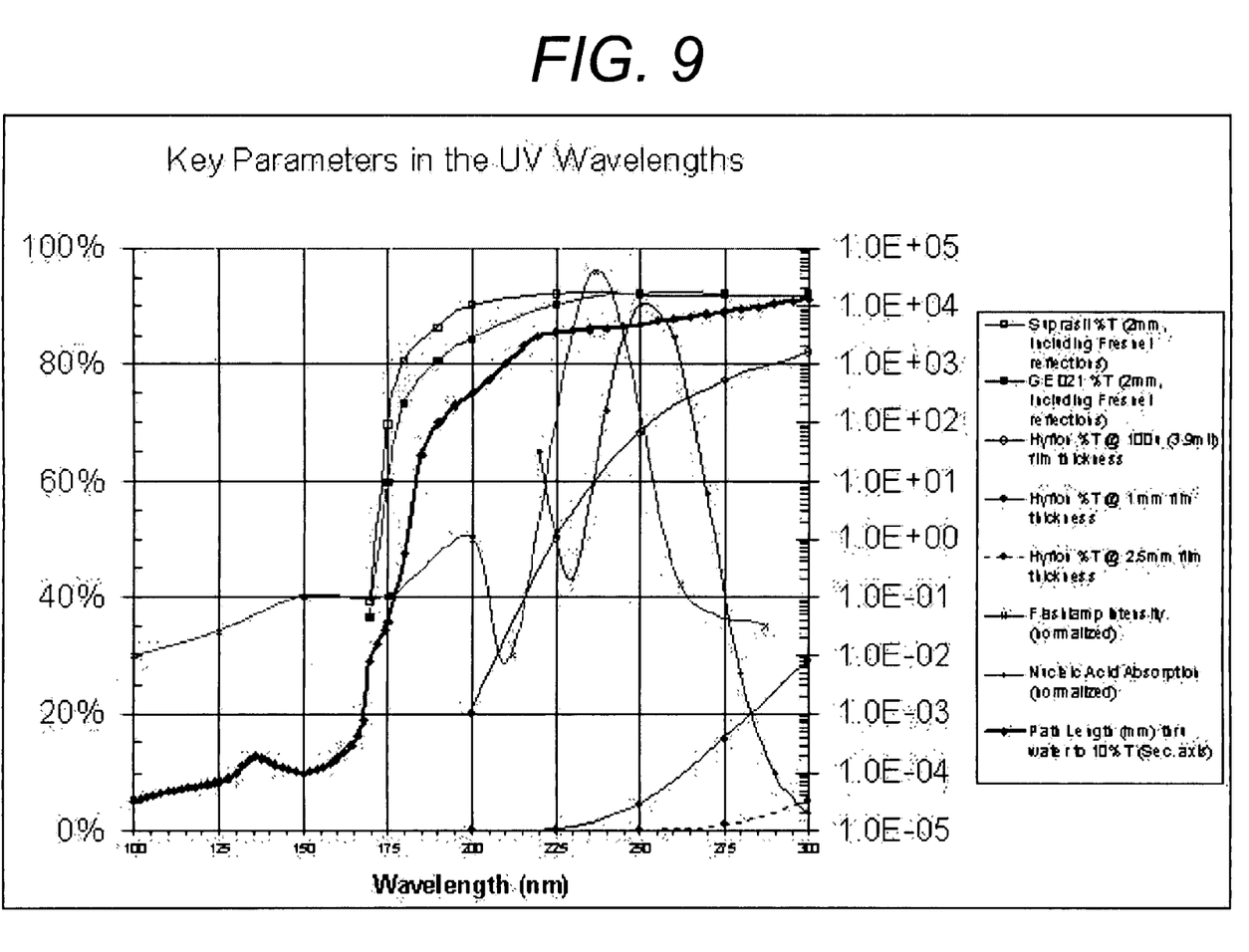
FIG. 9 depicts the characteristics of a xenon flash lamp, water, and various materials (glass, fluoropolymer, and nucleic acid) over UV wavelengths

FIG. 9 shows wavelength-based plots for flashlamp excitation and nucleic acid absorption in the ultraviolet region of the electromagnetic spectrum. FIG. 9 also details the ultraviolet absorption of UV-grade glasses such as Suprasil from Heraeus and '021 grade' and polymer materials such as Hyflon tubing from Ausimont. Details for the Ausimont tubing includes data for tubing having 0.1 mm, 1 mm, and 2.5 mm thickness respectively.

There are other high intensity UV sources beyond flashlamps known in the art, such semiconductor sources can be found at the Defense Advanced Research Projects Agency (DARPA) Semiconductor UV Optical Sources (SUVOS) website, http://www.darpa.mil/mto/suvos/summaries.html. Semiconductor sources are especially applicable to portable embodiments of the present invention, such as the canteen shown in FIG. 8.

Figure 10:
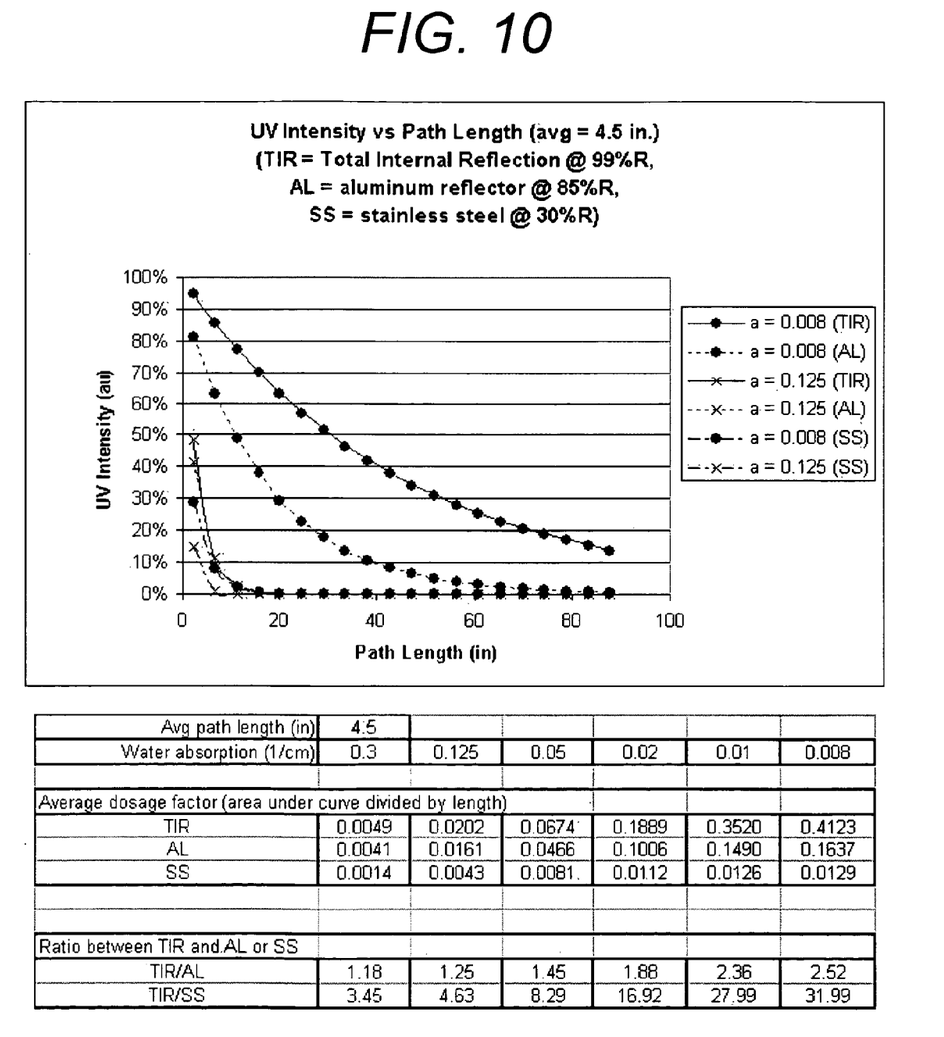
FIG. 10 shows the attenuation of UV intensity over distance as it travels through various types of reflective containers with an average path length of 4.5 inches.
Figure 11:
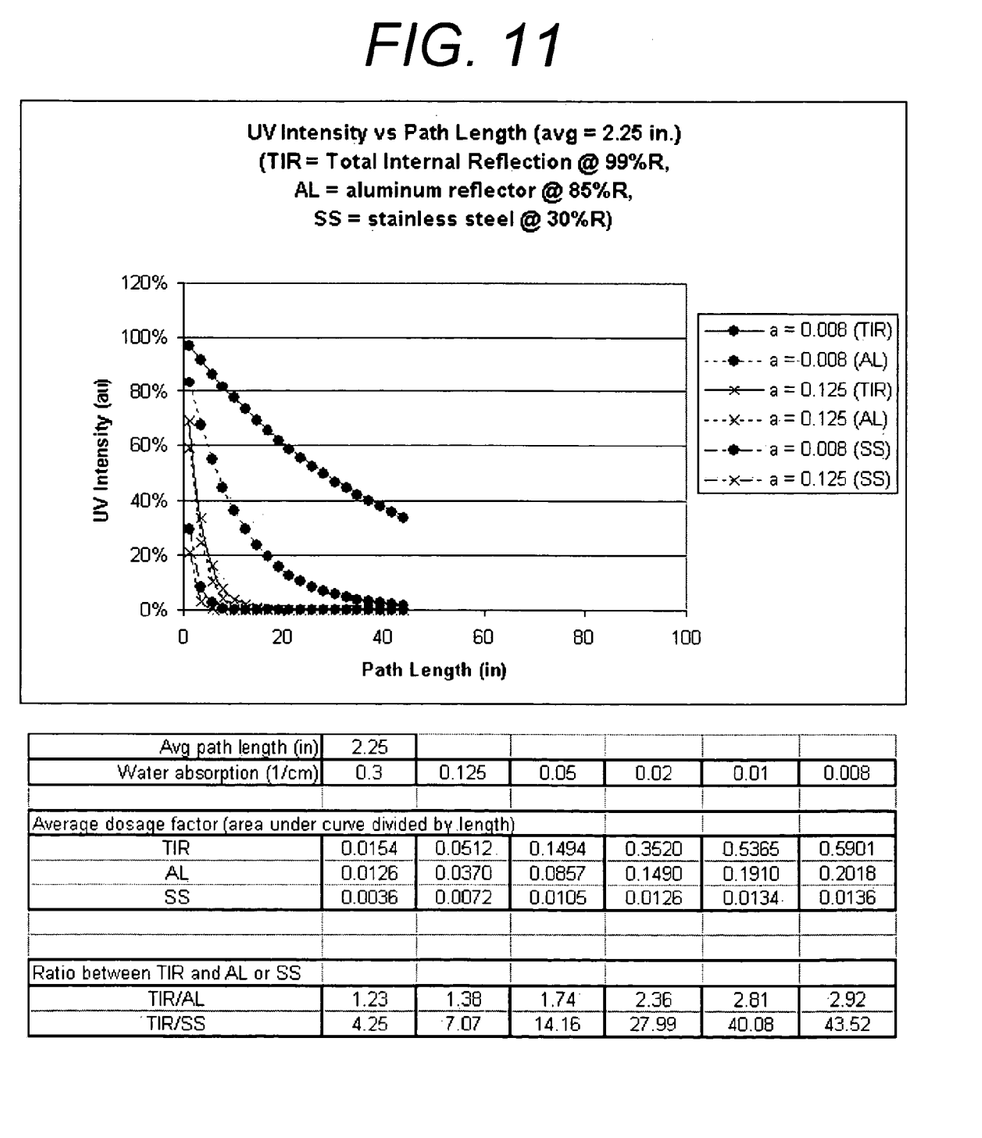
FIG. 11 shows the attenuation of UV intensity over distance as it travels through various types of reflective containers with an average path length of 2.25 inches.

Refer now to FIGS. 10 and 11 which illustrate the key design parameters for three sidewall configurations that are applicable to certain embodiments of the present invention. The selected sidewall configurations considered the effects of near-lossless TIR effect as well as mirror reflections from aluminum and stainless steel. In addition, variable water UV absorption coefficients of 0.008/cm and 0.125/cm repesctively were considered where such absorption was due to biological content only. For simplicity, losses due to natural absorption of UV within water are disregarded.

It thus is obvious to see that the area under each curve, shown in FIGS. 10 and 11, gives a visual indication of how the optical characteristics of a vessel effect the UV dosage efficacy (i.e. dosage per electrical watt of input power) independent of other factors discussed previously.

An average dosage calculation was made for each configuration of near-loss TIR and wall material, shown in FIG. 10 by multiplying the intensity at each interval by the length of the interval, computing the sum over an 87.75" path length, and then dividing the sum by 87.75 inches.

In FIG. 10 there is shown a graph illustrating the effects of sidewall reflection over the path length where UV radiation interacts with the fluid, such as water, that is being disinfected. This graph assumes the UV radiation is launched from a point in the center of a hypothetical fluid vessel, makes its first interaction with the sidewall at a distance of 2.25 inches, and thereafter interacts with the sidewall every 4.5 inches (these dimensions selected as a rough estimate of the average path length of a ray within an approximately 3-inch inside diameter vessel.

FIG. 11 is identical to FIG. 10 with the exception that the average path length has been changed from 4.5 inches to 2.25 inches.

ALTERNATE EMBODIMENTS

Alternate embodiments may be devised without departing from the spirit or the scope of the invention. For example, water within coiled tubing can be disinfected by ultraviolet radiation contained by total internal reflection using equipment that can be scaled up or down to many purification applications. Also, fluids other than water can be purified using the present invention.

What is claimed is:

1. An apparatus for disinfecting a fluid, said apparatus comprising:

a chamber having exterior walls, at least one inlet and one outlet, wherein the fluid enters the chamber through the inlet and exits through the outlet, and an optically transmissive window forming at least a portion of one of said exterior walls; and a lamp adapted to generate high intensity ultraviolet (UV) radiation, said lamp positioned adjacent said window for transmitting said UV radiation into said chamber;

said chamber includes an inner transmissive tube surrounded by an outer containment vessel spaced from said inner transmissive tube by a gap, said gap containing a material having an index of refraction in the ultraviolet region smaller than the index of refraction in the ultraviolet region of said walls of said chamber;

said tube and said gap define walls of said chamber;

wherein said ultraviolet radiation is guided through the chamber substantially via total internal reflection at said walls of said chamber;

wherein said gap comprises a vacuum.

2. The apparatus of claim 1, wherein said chamber comprises a hollow helical coil, and wherein said coil has a ratio of its bend-radius to the average radius of its cross section of greater than 5:1.

3. The apparatus of claim 1, wherein said outer containment vessel is of a metal with a reflective inner wall surface surrounding the inner transmissive tube.

4. The apparatus of claim 3 wherein said reflective inner wall surface is spaced apart from said inner transmissive tube a distance sufficient to avoid interfering with said total internal reflections, said reflective inner wall surface reflecting back to said inner transmissive tube substantially any ultraviolet radiation that escapes said inner transmissive tube wall.

5. The apparatus of claim 4 wherein said inner transmissive tube is of UV grade fused silica.

6. An apparatus for disinfecting a fluid, said apparatus comprising:
- a chamber comprising a hollow helical coil having walls, at least one inlet and one outlet, wherein the fluid enters the chamber through the inlet and exits through the outlet, and an optically transmissive window,
- a high intensity source of ultraviolet (UV) radiation positioned adjacent said window for transmitting said UV radiation into said chamber; and
- wherein said ultraviolet radiation is guided through the chamber substantially via total internal reflection and radiation from said source of ultraviolet radiation is coupled into said coil via a non-UV absorbing coupling prism.

7. An apparatus for purifying a fluid using ultraviolet (UV) energy, said apparatus comprising:
- a tube through which the fluid to be purified flows, said tube having exterior walls and comprising a non-UV absorbing material;
- means encompassing at least a portion of said tube and having a lower refractive index than said tube;
- a lamp adapted to generate of UV energy; and
- a window surface defining at least a portion of said exterior walls and through which the UV energy from said lamp is coupled into said fluid within said tube, whereby said UV energy is propagated within the length of said tube via total internal reflection;
- wherein said tube has a polygonal cross sectional shape.

8. The apparatus of claim 7 wherein said means comprises means defining a gap.

9. The apparatus of claim 8 wherein said gap encloses one of air and a vacuum.

10. The apparatus of claim 9 wherein said gap encompasses a lower portion of said tube.

11. The apparatus of claim 7 further comprising a metallic reflector surrounding said tube, said metallic reflector causing UV energy scattered by air bubbles within said fluid to be directed back into said fluid within said tube.

12. The apparatus of claim 11 wherein metallic reflector comprises aluminum.

13. The apparatus of claim 8 comprising an outer containment vessel surrounding said tube and defining said gap.

14. The apparatus of claim 7 wherein said tube comprises UV-grade quartz.

15. An apparatus for disinfecting a fluid, said apparatus comprising:
- a chamber defining a fluid flowpath, said chamber having exterior walls and a light pipe region extending for at least a portion of the fluid flowpath;
- an optically transmissive window forming at least a portion of said exterior walls of said chamber; and
- a source of high intensity ultraviolet (UV) radiation, said source configured to direct said UV radiation through said window and into said light pipe region of said chamber, said light pipe region directing the UV radiation substantially along the fluid flowpath via total internal reflection.

16. The apparatus of claim 15, wherein the light pipe region includes an inner tube and an optical cladding tool that defines a concentric gap adjacent the inner tube.

17. The apparatus of claim 16, wherein the inner tube is comprised of UV-grade fused silica and the concentric gab is comprised of a vacuum.

* * * * *